(12) United States Patent
Overes

(10) Patent No.: US 10,398,564 B2
(45) Date of Patent: Sep. 3, 2019

(54) EXPANDABLE SPINAL IMPLANT

(71) Applicant: 41MEDICAL AG, Bettlach (CH)

(72) Inventor: Tom Overes, Langendorf (CH)

(73) Assignee: 41MEDICAL AG, Bettlach (CH)

( * ) Notice: Subject to any disclaimer, the term of this patent is extended or adjusted under 35 U.S.C. 154(b) by 135 days.

(21) Appl. No.: 15/559,044

(22) PCT Filed: Mar. 23, 2015

(86) PCT No.: PCT/CH2015/000047
§ 371 (c)(1),
(2) Date: Sep. 16, 2017

(87) PCT Pub. No.: WO2016/145542
PCT Pub. Date: Sep. 22, 2016

(65) Prior Publication Data
US 2018/0071110 A1 Mar. 15, 2018

(30) Foreign Application Priority Data
Mar. 18, 2015 (CH) .......................... 379/15

(51) Int. Cl.
*A61F 2/44* (2006.01)
*A61F 2/46* (2006.01)
*A61F 2/30* (2006.01)

(52) U.S. Cl.
CPC ............ *A61F 2/4425* (2013.01); *A61F 2/447* (2013.01); *A61F 2/4455* (2013.01); *A61F 2/4465* (2013.01); *A61F 2/4611* (2013.01); *A61F 2/442* (2013.01); *A61F 2002/3054* (2013.01); *A61F 2002/3055* (2013.01); *A61F 2002/30179* (2013.01); *A61F 2002/30378* (2013.01); *A61F 2002/30471* (2013.01); *A61F 2002/30507* (2013.01); *A61F 2002/30523* (2013.01); *A61F 2002/30525* (2013.01); *A61F 2002/30545* (2013.01); *A61F 2002/30579* (2013.01); *A61F 2002/30593* (2013.01); *A61F 2002/30616* (2013.01); *A61F 2002/4629* (2013.01); *A61F 2310/00023* (2013.01)

(58) Field of Classification Search
CPC ....................................... A61F 2/4425
See application file for complete search history.

(56) References Cited

U.S. PATENT DOCUMENTS 7,087,055 B2 * 8/2006 Lim ..................... A61B 17/025
606/198
2005/0021144 A1  1/2005 Malberg et al.
(Continued)

FOREIGN PATENT DOCUMENTS

EP   2 446 860 B1   5/2012
EP   2 777 633 A2   9/2014
(Continued)

*Primary Examiner* — Andrew Yang
(74) *Attorney, Agent, or Firm* — Maschoff Brennan

(57) ABSTRACT

The present application relates to an expandable spinal implant (1) comprising two elongated implant members (20, 30). The implant members (20, 30) are rotatably coupled to a central base portion (10) and comprise a first end with an axis of rotation and circumferentially arranged gear teeth (23, 33). The gear teeth (23) of the first elongated implant member (20) is interlocked into said gear teeth (33) of the second elongated implant member (30).

12 Claims, 4 Drawing Sheets

(56) References Cited

U.S. PATENT DOCUMENTS

| | | |
|---|---|---|
| 2006/0195089 A1 | 8/2006 | LeHuec et al. |
| 2007/0225808 A1 | 9/2007 | Warnick |
| 2009/0048676 A1 | 2/2009 | Fabian, Jr. |
| 2010/0222816 A1 | 9/2010 | Gabelberger et al. |
| 2012/0029639 A1 | 2/2012 | Blackwell et al. |
| 2012/0197299 A1 | 8/2012 | Fabian, Jr. |
| 2012/0271422 A1 | 10/2012 | Miller et al. |
| 2013/0079883 A1* | 3/2013 | Butler .................. A61F 2/4425 623/17.16 |
| 2015/0257894 A1 | 9/2015 | Levy et al. |

FOREIGN PATENT DOCUMENTS

| | | |
|---|---|---|
| WO | 2007/121320 A2 | 10/2007 |
| WO | 2009/098536 A1 | 8/2009 |
| WO | 2011/141869 A1 | 11/2011 |
| WO | 2012/115631 A1 | 8/2012 |

\* cited by examiner

EXPANDABLE SPINAL IMPLANT

TECHNICAL FIELD

The invention relates to an expandable spinal implant to be arranged between two adjacent vertebral bodies.

BACKGROUND

Low back pain is a common disease for example caused by herniated discs, compressed nerve roots, degenerative discs or joint disease.

If a patient has this severe pain and does not respond to conservative treatment, spinal fusion is an option to eliminate the pain. Spinal fusion is a surgical technique, wherein two or more vertebrae are joined together. Spinal fusion interventions are also performed to correct back deformities.

With inter-body fusion often an intervertebral spacer or device is placed between the involved vertebrae after removal of the intervertebral disc. The intervertebral device corrects the spine alignment and restores the disc height.

Common intervertebral devices are made from titanium alloys or polyetheretherketone (PEEK). Often these devices comprise pockets that can be filled with bone graft material or artificial graft substitute. The fusion itself takes place when the bone of the endplates grows into and through the intervertebral device. Finally both vertebrae are grown together. Often, additionally, a pedicle system provides additional posterior stabilisation. Intervertebral fusion devices can be implanted with various approaches, for example from the anterior, the posterior or the lateral side.

Over the past years minimal invasive techniques have been introduced. The advantages of the minimal invasive techniques are less soft tissue trauma resulting in a faster recovery. Other complications are reduced as well. In minimal invasive techniques the implant is brought into position between the vertebrae through a small incision with small instruments. Still the intervertebral device must have a sufficient large foot-print to translate the forces between the vertebrae before complete fusion has taken place. If a device is too small, it will sink into or break through the endplate of the vertebra, and the initially restored height is lost.

Combining advantages of the minimal invasive surgery approaches with well supporting intervertebral devices with large foot-print, a device would be required that can be brought into place through a small incision, and in a second step is expanded to a larger size.

Various embodiments of such devices are known in the art. For example, WO 2009/098536 (Calvosa Giuseppe) discloses an intervertebral distractor comprising stop members and which may be percutaneously implanted. The distractor comprises an elongated body adapted to provide an interspinous support between two adjacent spinous processes as well as a first and a second couple of mobile stabilizers which are adapted to rotate from a closed position to a spread apart position. Further, the distractor includes means for bringing said stabilizers from the closed position into the spread apart position, wherein said means are movable along a longitudinal axis of said distractor and being coupled to one end of each of said stabilizers to rotate said stabilizers from said closed position to said spread apart position.

U.S. 2009/0048676 A1 (Henry Fabian JR) describes an implant comprising two members being pivotal relative to each other and each comprising two limbs. The implant may be inserted into a vertebral space in a first non-expanded configuration, where all limbs are adjacent to each other, and which may then subsequently be deployed to a second expanded configuration having a larger foot-print, where the limbs are separated from each other. The implant may further comprise a locking mechanism used to lock the position of the first member relative to the second member. Deployment of the implant from the first configuration to the second configuration is performed by a cable which may be pulled by a surgeon such as to expand the implant.

U.S. 2012/0029639 discloses interbody spinal implants being implantable into a patient in a first orientation having a reduced height and then rotated to a second orientation which extends the height of the implant.

The implants known in the art have the disadvantage that the expansion of the different implant parts may not be equal due to different forces acting on each part. For example, the use of a cable exerts a maximal force onto one part which is directly coupled to the cable, while the force exerted on other parts may be diminished by external forces acting on these parts.

SUMMARY OF THE INVENTION

It is the object of the invention to create an expandable spinal implant that allows a uniform movement of any part of the implant, thus yielding a uniform deployment of the implant in the intervertebral space between adjacent vertebrae.

The solution of the invention is specified by the features of claim 1. According to the invention the expandable spinal implant comprises a first elongated implant member and a second elongated implant member. Each of said elongated implant members is rotatably coupled to a central base portion and comprises a first end with an axis of rotation and circumferentially arranged gear teeth. The gear teeth of the first implant member are interlocked into the gear teeth of the second implant member.

By rotating one of said two elongated implant members around its axis of rotation, the other elongated implant member is also moved around its axis of rotation. The transmission of the rotation movement by means of a gear tooth system ensures a uniform transmission of the rotation movement and hence allows a uniform deployment of both elongated implant members.

The expandable spinal implant according to the present invention is expandable in a plane which is essentially parallel to the surfaces of the vertebral bodies facing towards the intervertebral space the expandable spinal implant is to be implanted into. Hence, expansion of the inventive expandable spinal implant only results in an expansion of the overall foot-print of the expandable spinal implant while the distance between the adjacent vertebrae is not increased.

The interlocking of the gear teeth of the first elongated implant member with the gear teeth of the second elongated implant member results in a kind of gear or transmission system, wherein upon rotation of one of the two elongated implant member in one direction, the other elongated implant member is rotatably moved into an opposite direction.

Preferably, both elongated implant members have gear teeth which are arranged at the same distance from the axis of rotation, i.e. the gear ratio between the elongated implant members is 1:1. Hence, rotation of one of said elongated implant member by a specific angle will provoke a rotation of the other elongated implant member by the same angle.

Alternatively, the distance between the teeth to the axis of rotation of at least one of the elongated implant members may be chosen to be unequal to the distance of the other elongated implant member. This results in different rotational speeds of the elongated implant members, i.e. to a gear ratio which is higher or lower than 1:1.

Provision of gear teeth allows the expansion of the expandable spinal implant by exerting a pulling force on any of the two elongated implant members, as rotation of any of said elongated implant members will exert a rotational force onto the other elongated implant member.

The axes of rotation of both elongated implant members are preferably parallel to each other. The gear teeth are arranged around said axes along at least a portion of a circle. Preferably, the gear teeth are arranged around a half circle or a quadrant of a circle, said circle having its centre located on the axis of rotation of the respective elongated implant member.

The elongated implant members preferably have a base area which is in the form of a trapezoid, more preferably of a right angle trapezoid. Further preferably, at least one corner area of each of said elongated implant members is rounded such as to ease the insertion of the expandable spinal implant without causing any irritation to the annulus. The circumferentially arranged gear teeth are preferably located on one of the smaller sides of the elongated implant members.

The elongated implant members each preferably have a lower surface and an upper surface configured to contact bone of two adjacent vertebral bodies. Said lower and said upper surface are spaced from each other by a thickness which preferably corresponds to the natural height of an intervertebral disc. Both surfaces may be arranged parallel to each other, however preferably, the thickness of the elongated implant members varies from one end of the expandable spinal implant which is to be arranged on a ventral side of the intervertebral space to the side which is to be arranged on a dorsal side of the intervertebral space. This allows conforming the shape of the expandable spinal implant to the natural shape of the intervertebral space.

Said upper surface and said lower surface preferably include a structure which enhances the friction between the surfaces and the bone of the adjacent vertebral bodies. Said structure may e.g. comprise a multitude of ribs, burls, pyramid shape protrusions or the like. Such a structure enhances the friction between the elongated implant members and the vertebral bone, hence safely anchoring the expandable spinal implant in the intervertebral space.

The central base portion constitutes the attachment point of both elongated implant members. Hence, each elongated implant member is rotatably coupled to said central base portion by means of its rotation axis.

Preferably, said elongated implant members each include a recess into which a part of the central base portion may be inserted. This allows configuring the expandable spinal implant with flush surfaces. More preferably, said recess is arranged centrally between the upper surface and the lower surface of each of said elongated implant members. This allows to insert parts of the central base portion into said recesses and to rotatably couple the central base portion on both sides with each of said elongated implant members by means of a peg or pin, hence increasing the stability of the coupling between the central base plate and each of the elongated implant members. Preferably, circumferentially arranged gear teeth are arranged on both sides of said recess.

Preferably, the expandable spinal implant is made of titanium or a titanium alloy. Further preferably, the expandable spinal implant may be made of a biocompatible polymer, most preferably of polyetheretherketone (PEEK) or of fiber reinforced polyetheretherketone. Further, the expandable spinal implant may be made of a combination of materials.

Preferably, the base portion is a body in the form of a segmental arc and said elongated implant members are coupled to the base portion at an apex of said segmental arc.

Provision of the base portion and the elongated implant members in the form of segmental arcs has the advantage that the expandable spinal implant may be easily inserted between two adjacent implant bodies, as the arced shape substantially conforms to the curvature of the rim of the spinal bodies.

As understood herein, a segmental arc is a segment of a curve, especially of a circle. The segmental arc thereby spans less than 180°, i.e. less than a semicircle. Alternatively, the segmental arc may also be in the form of a segment of an ellipse, a so-called elliptical arc. By coupling the elongated implant elements to the apex, both elongated implant elements are symmetrically arranged on said central base portion.

In a preferred embodiment, the elongated implant members are in the shape of a segmental arc and substantially abut with said base portion along their entire length in an initial an unexpanded configuration. This allows providing an expandable spinal implant having a very small footprint in the unexpanded configuration. Hence the size of the expandable spinal implant for implantation is small, allowing the insertion of the expandable spinal implant through an incision with minimal dimensions.

Preferably, said elongated implant members and said central base portion form a substantially X-shaped footprint in an expanded configuration. As the central base portion and the elongated implant members preferably are in the form of a segmental arc, the "legs" of the X-shape will be curved. The centre of the X-shape is thereby defined by the apex of the central base portion to which the elongated implant members are coupled. Provision of such a configuration allows having a large footprint of the expandable spinal implant in the expanded configuration.

In an alternatively preferred embodiment, the elongated implant members and the central base portion are substantially straight and form a substantially K-shaped footprint in an expanded configuration. Preferably, the elongated implant members are coupled to the central base portion at a location which is in the middle of the length of said central base portion, such that the elongated implant members are symmetrically arranged onto said central base portion.

The expandable spinal implant preferably comprises at least one pocket for receiving bone graft material. Preferably said at least one pocket is arranged in one of the elongated implant members and spans the entire thickness of said elongated implant member, i.e. the pocket is in the form of a bore or hole spanning the entire thickness of said elongated implant member. Provision of such a pocket allows applying bone graft material linking both vertebrae together. This enhances the ingrowth of bone through the expandable spinal implant. Preferably, each of said elongated implant members comprises at least one pocket for receiving bone ingrowth material.

Preferably, said expandable spinal implant comprises elongated implant members of unequal length. This allows tailoring the expandable spinal implant to different intervertebral spaces, e.g. depending on the type of vertebrae adjacent said intervertebral space. For example, the configuration of the lengths of the elongated implant members may be different if the expandable spinal implant is to be implanted between thoracic vertebrae or between lumbar vertebrae.

Preferably, the expandable spinal implant comprises a dowel having a ball head on one end, said ball head cooperating with a first channel located on the inside of the first elongated implant member, such as to impart motion onto said first elongated implant member for rotating said first elongated implant member relative to said central base structure around its axis of rotation.

Preferably, said dowel is cylindrical and said ball head has a first diameter. The first channel is preferably cylindrical and has a diameter which corresponds to the first diameter of the ball head. Preferably, the ball head is form-fittingly engaged within said channel, such that pulling and pushing forces acting on said dowel are transmitted onto said first elongated implant member.

This provides a simple and easy to use drive for the expandable spinal implant, as a linear movement of the dowel will exert a pulling or pushing force on said first elongated implant member, resulting in a rotational movement of said first elongated implant member. Alternatively, the dowel may comprise a single protrusion which engages into a single groove provided on said one elongated implant member.

Further, any suitable type of form-fit interaction may be used for cooperation of said dowel with the elongated implant member.

Preferably, the dowel is arranged in a second channel provided in said central base portion, said second channel having an opening allowing the insertion of the instrument by a surgeon, such as to push or pull the dowel to move it relative to said central base portion.

Preferably, said dowel comprises a drive at a second end arranged opposite of said first end, such that an instrument to move said dowel may be inserted into said drive. More preferably, an outer thread is arranged on said second end, said outer thread cooperating with a matching inner thread provided in said central base portion of the expandable spinal implant, preferably in said second channel. Hence, by imparting a turning motion to said dowel, the dowel will be linearly moved relative to said central base portion, thus imparting a pulling or pushing force onto said elongated implant member by means of the form-fit interaction of the two ball head within the first channel.

Preferably, each of the two elongated implant members as well as the central base portion comprises a lower surface and an upper surface, said upper surfaces and said lower surfaces being flush with each other.

Hence, both elongated implant members as well as the central base portion may contact and thus support adjacent vertebral bodies, as they form a contiguous upper and lower plane. Preferably, the central base portion comprises at least one part with surfaces which are not flush with the lower and upper surfaces of the elongated implant members, but spaced apart from these. Preferably, said at least one part is located at the apex of the segmental arc of the central base portion. The two elongated implant members are preferably coupled to the at least one part, while the at least one part may be engaged into the recess of said elongated implant members.

Preferably, said upper and said lower surfaces are arranged at an angle to each other. Said angle more preferably is from 0° to 15°.

The two surfaces are located on the two sides of the elongated implant members intended to be in contact with the bone of adjacent vertebrae. By varying the angle of the upper and lower surfaces relative to each other allows to restore the natural lordotic or kyphotic curvature of the spine.

Preferably, the lower surfaces and the upper surfaces of said elongated implant members and of said central base portion are parallel to each other.

The present application further relates to a kit comprising multiple expandable spinal implants according to the present invention, wherein the implants have incremental thicknesses between 8 and 20 mm. Hence, a surgeon may always select the expandable spinal implant having an appropriate thickness for the intervertebral space to be treated.

Further preferably, the kit may also comprise multiple expandable spinal implants according to the present invention having different combinations of elongated implant member lengths and/or elongated implant member widths.

As understood herein, the thickness of the expandable spinal implant is understood as the maximal distance between the upper and lower surfaces of said elongated implant members and of said central base portion.

Preferably, the kit comprises expandable spinal implants having varying angles between the lower surfaces and the upper surfaces of the elongated implant members and of the central base portion. This allows a surgeon to select an implant which has an optimal angle to restore the natural lordotic or kyphotic curvature of a patient's spine. Preferably, the angles vary from 1° to 15°.

Other advantageous embodiments and combinations of features come out from the detailed description below and the totality of the claims.

BRIEF DESCRIPTION OF THE DRAWINGS

The drawings used to explain the embodiments show.

In the figures, the same components are given the same reference symbols.

PREFERRED EMBODIMENTS

Figure 1:
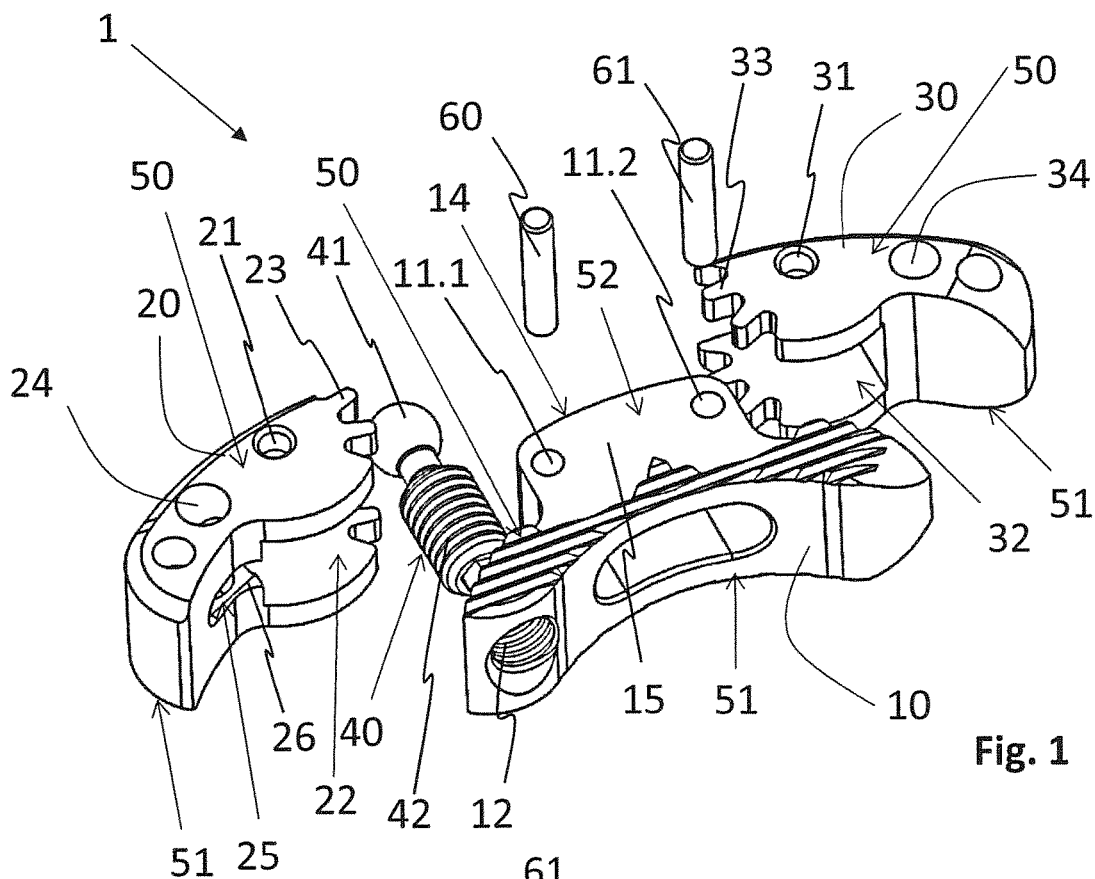
FIG. 1 a first embodiment of an expandable spinal implant according to the present invention in an exploded view.

FIG. 1 shows a first embodiment of the expandable spinal implant 1 in an exploded view. The expandable spinal implant 1 comprises a first elongated implant member 20, a second elongated implant member 30, a central base portion 10, two hinge-pins 60, 61 and a dowel 40.

Each of the elongated implant members 20, 30 comprises an axis of rotation at a first end. Each axis of rotation is defined by a corresponding bore 21, 31 into which one of the two hinge-pins 60, 61 is inserted. Furthermore, the elongated implant members 20, 30 each comprise a recess 22, 32 extending through the elongated implant member 20, 30 and intersecting with the bores 21, 31 wherein each recess 22, 32 is substantially perpendicularly arranged in reference to the respective axis of rotation defined by each bore 21, 31. Said first ends of the elongated implant members 20, 30 are of a half cylindrical shape and comprise a set of gear teeth 23, 33, circumferentially arranged around the axis of rotation defined by bores 21, 31. The gear teeth 23, 33 are arranged on both sides of the recesses 22, 32. Towards a second end, the elongated implant members 20, 30 each comprise a pocket 24, 34 extending from a top surface 50 to a bottom surface 51, wherein the pockets 24, 34 are shaped to receive bone graft material or a bone graft substitute, to promote bone ingrowth. Both elongated implant members 20, 30 are in the general shape of a segmental arc.

The central base portion 10 is a block shaped element in the general shape of a segmental arc which comprises, like the elongated implant members 20, 30, a top surface 50 and a bottom surface 51. At the apex 14 of the segmental arc, the central base portion comprises a part 15 with a top side 52 and a bottom side 53 which are spaced apart from the upper surface 50 and the lower surface 51, respectively, of the central base portion 10. The part 15 comprises two substantially parallel through-bores 11.1, 11.2, extending form the top side 52 to the bottom side 53 of the part 15. Said through bores 11.1, 11.2 are configured to each receive one of the two hinge-pins 60, 61 such as to rotatably couple each of the elongated implant members 20, 30 to said central base portion 10.

The dowel 40 comprises a ball-head 41 and a threaded shaft 42. The ball-head 41 is engaged within a first channel 25 located on the inside of the first elongated implant member 20. The first channel 25 includes an opening 26 connecting said channel 25 to the outside and allowing the passage of the dowel 40 into said first channel 26. The threaded shaft 42 is engaged within a second channel 12 which comprises an internal thread cooperating with the threaded shaft 42.

Figure 2:
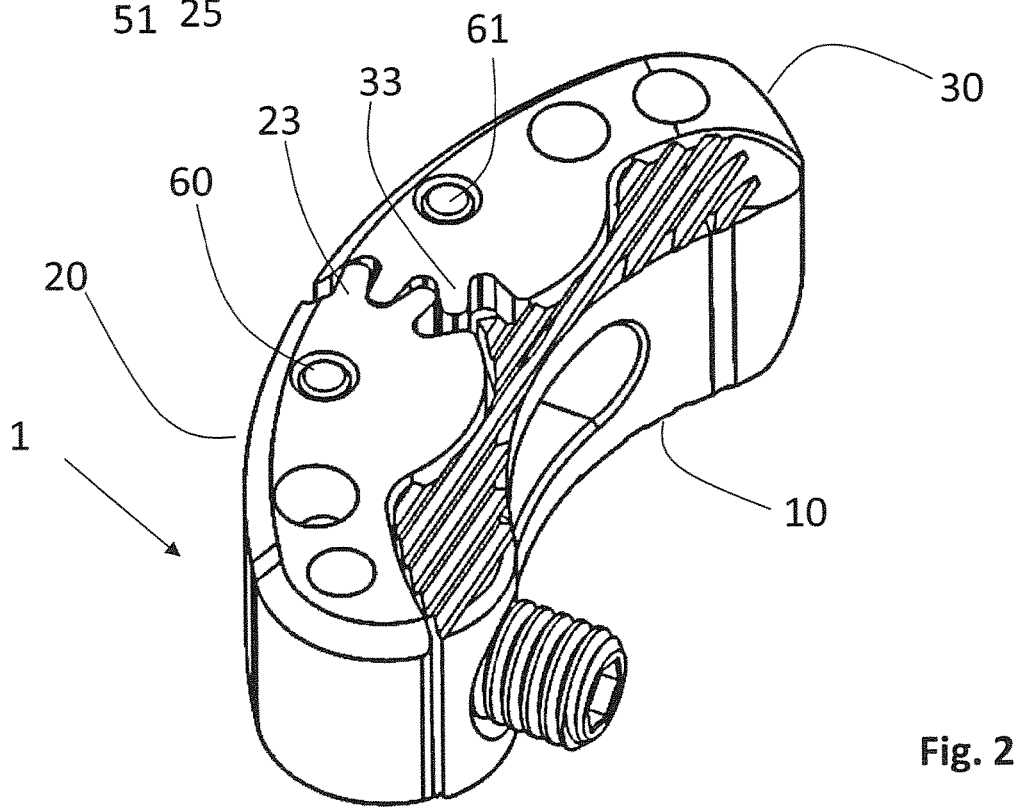
FIG. 2 the expandable spinal implant according to FIG. 1 in an assembled configuration.

FIG. 2 shows the expandable spinal implant 1 in an assembled state. The two elongated implant members 20, 30 are rotatably coupled to the central base portion 10 by means of the two hinge-pins 60, 61 which are introduced into the bores 21, 31 of the elongated implant members 20, 30, and through the through bores 11.1, 11.2 of the central base portion 10. The part 15 of the central base portion 10 is arranged within the recesses 22, 32 of the elongated implant members 20, 30. Both elongated implant members 20, 30 may only rotate around their rotation axis defined by the bores 21, 31. The sets of teeth 23, 33 are interlocked. As a result, upon actuation or rotation of the first elongated implant member 20, the second elongated implant member 30 will be actuated or rotated.

Note that the two elongated implant members 20, 30 are in the initial, unexpanded configuration. In this initial configuration, both elongated implant members 20, 30 abut onto the central base portion 10 along their entire length.

Figure 3A:
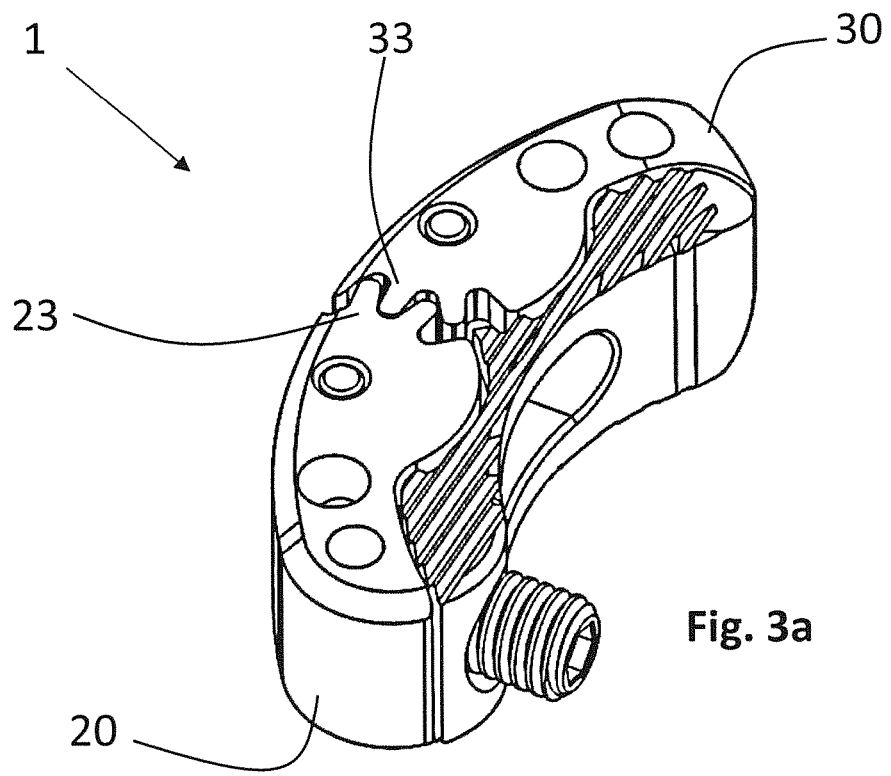
FIG. 3a, 3b the expansion of the expandable spinal implant according to FIG. 1.
Figure 3B:
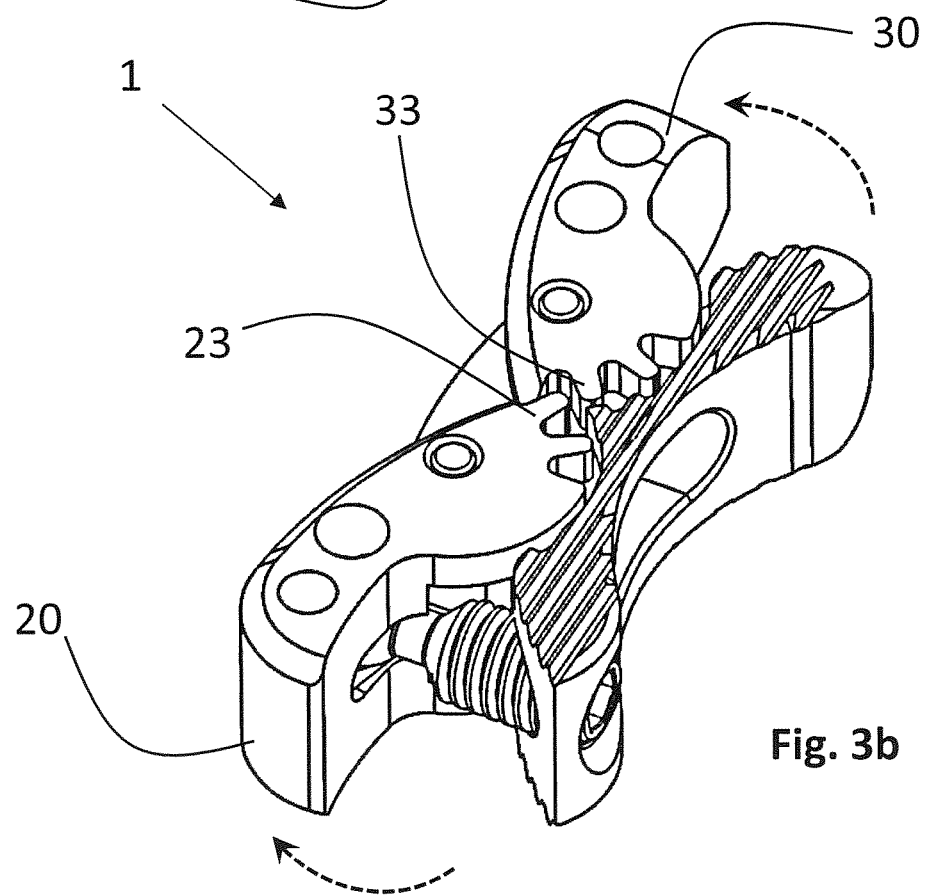

FIGS. 3a and 3b show the expansion of the expandable spinal implant 1 according to FIG. 2. In a first initial and unexpanded configuration, the elongated implant members 20, 30 are abutting the central base portion 10 on their entire length. The expandable spinal implant 1 has a substantially elongated, curved and narrow footprint in said first initial configuration, as shown in FIG. 3a. Upon actuation of the first elongated implant member 20, both elongated implant members 20, 30 rotate outwards, resulting in a second, expanded configuration as shown in FIG. 3b. This rotation is caused by the interaction of the gear teeth 23, 33 with each other. Hence, a rotation movement of one of said elongated implant members 20, 30 is transmitted by means of the gear teeth 23, 33 to the other elongated implant member 20, 30. In the second configuration the elongated implant members 20, 30 impart a generally X-shaped footprint to the expandable spinal implant 1.

In a variant, the elongated implant members 20, 30 may have a different length, for instance the first elongated implant member 20 may be longer than the second elongated implant member 30.

Figure 4A:
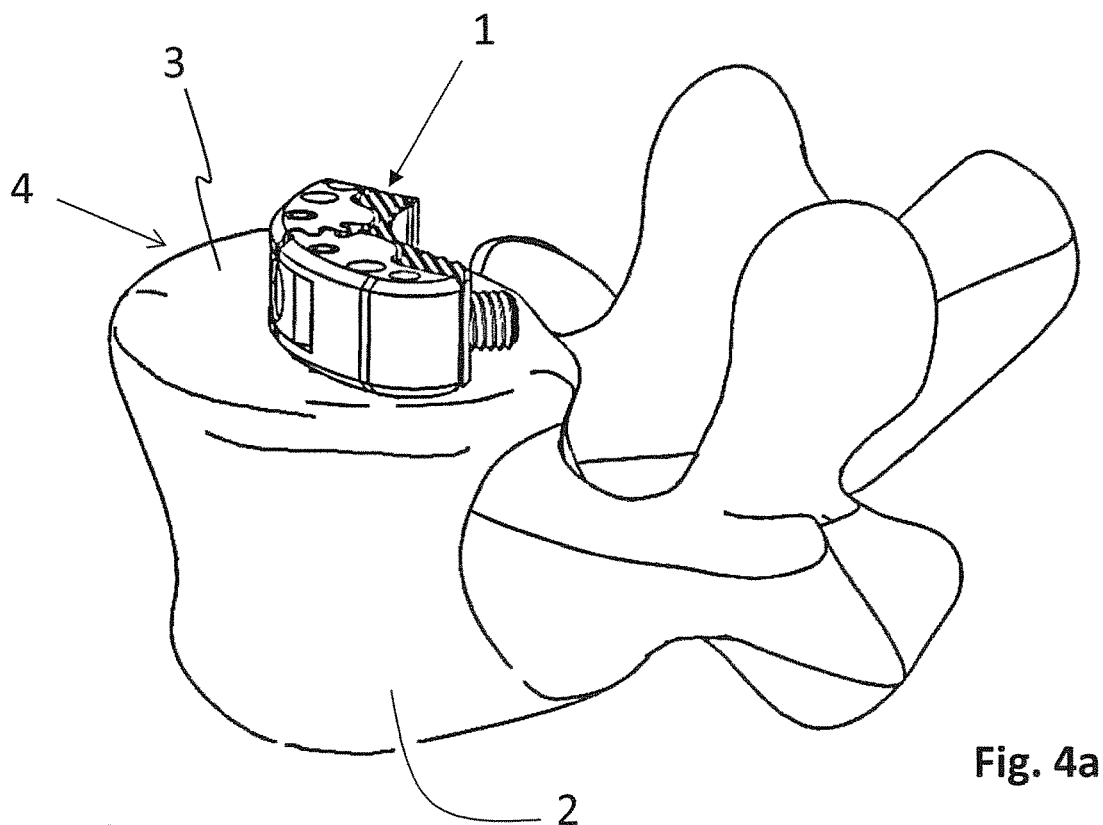
FIG. 4a, 4b the expandable spinal implant according to FIG. 1 arranged on a vertebral body.
Figure 4B:
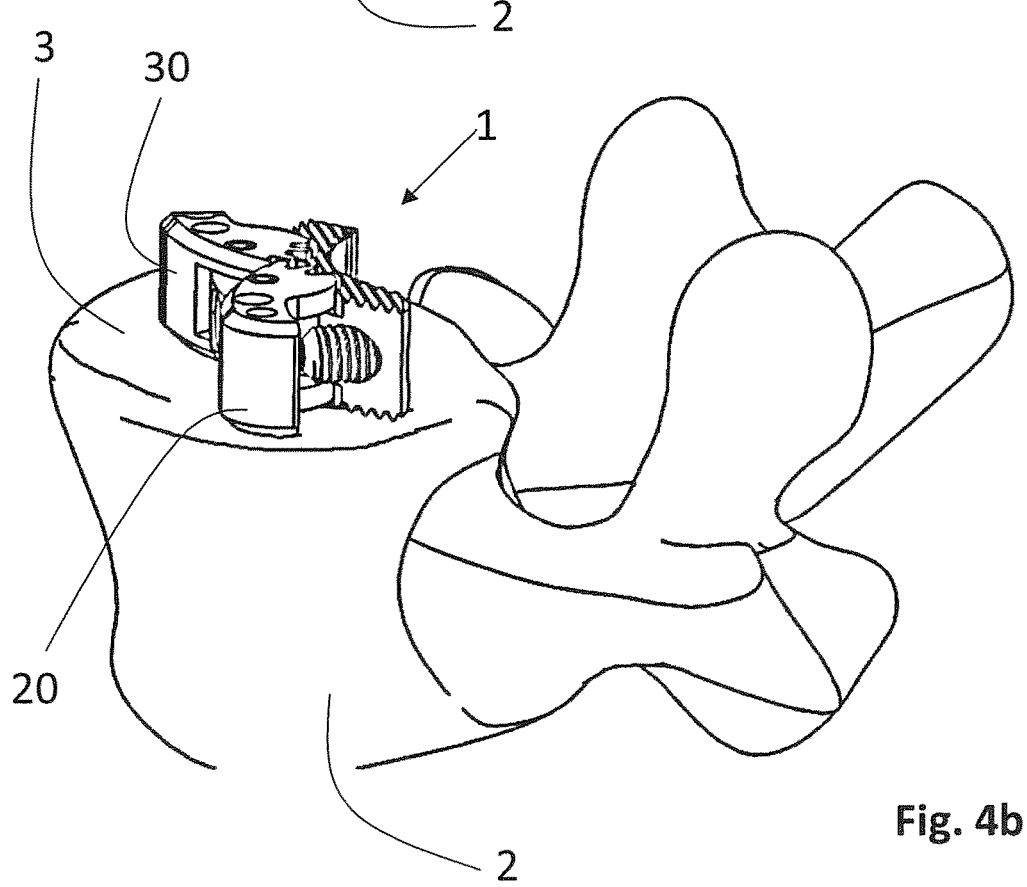

FIGS. 4a and 4b show the expandable spinal implant 1 arranged on a vertebral body 2. The expandable spinal implant 1 is thereby placed on the endplate 3 of the vertebral body 2 and occupies the intervertebral space 4 which would normally be occupied by the intervertebral disc. The adjacent vertebra on the other side of the intervertebral space 4 is not shown as it would cover the expandable spinal implant 1 in the perspective of the figure. FIG. 4a shows the expandable spinal implant 1 in the first, unexpanded configuration. In the second, expanded configuration, the elongated implant members 20, 30 are positioned close to the outer perimeter of the endplate 3 of the vertebral body 2, where the bone is denser, and withstands higher loads, as shown in FIG. 4b.

Figure 5A:
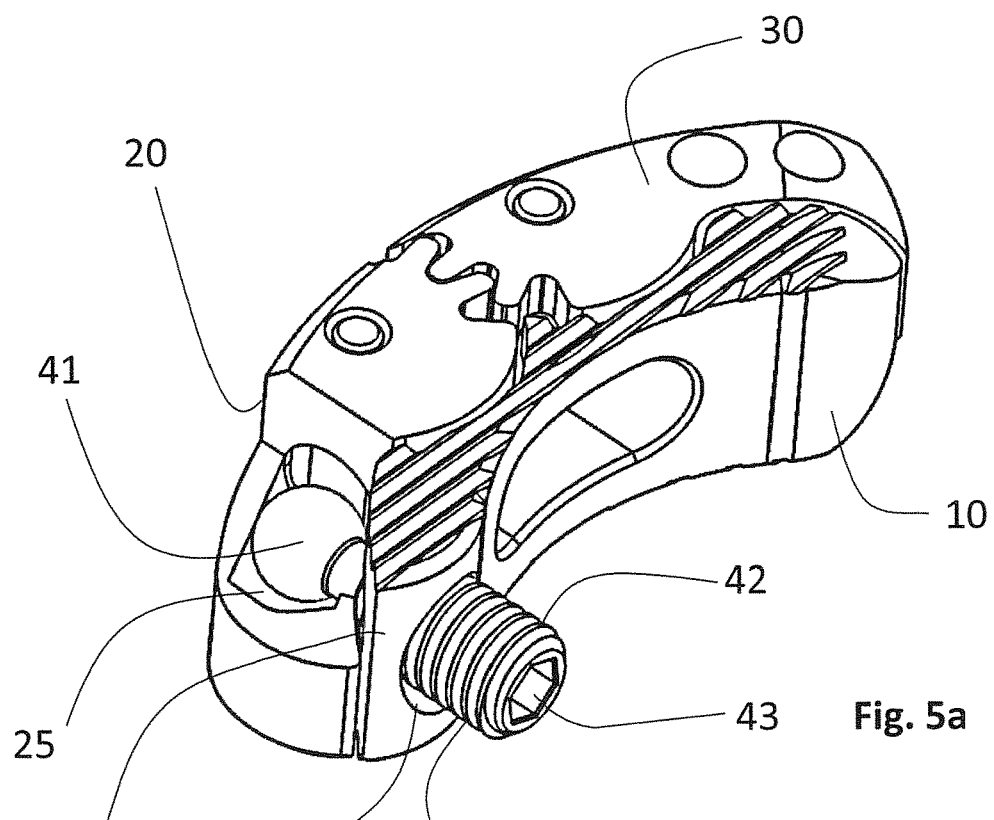
FIG. 5a-5b a second embodiment of an expandable spinal implant according to the present invention comprising a dowel.
Figure 5B:
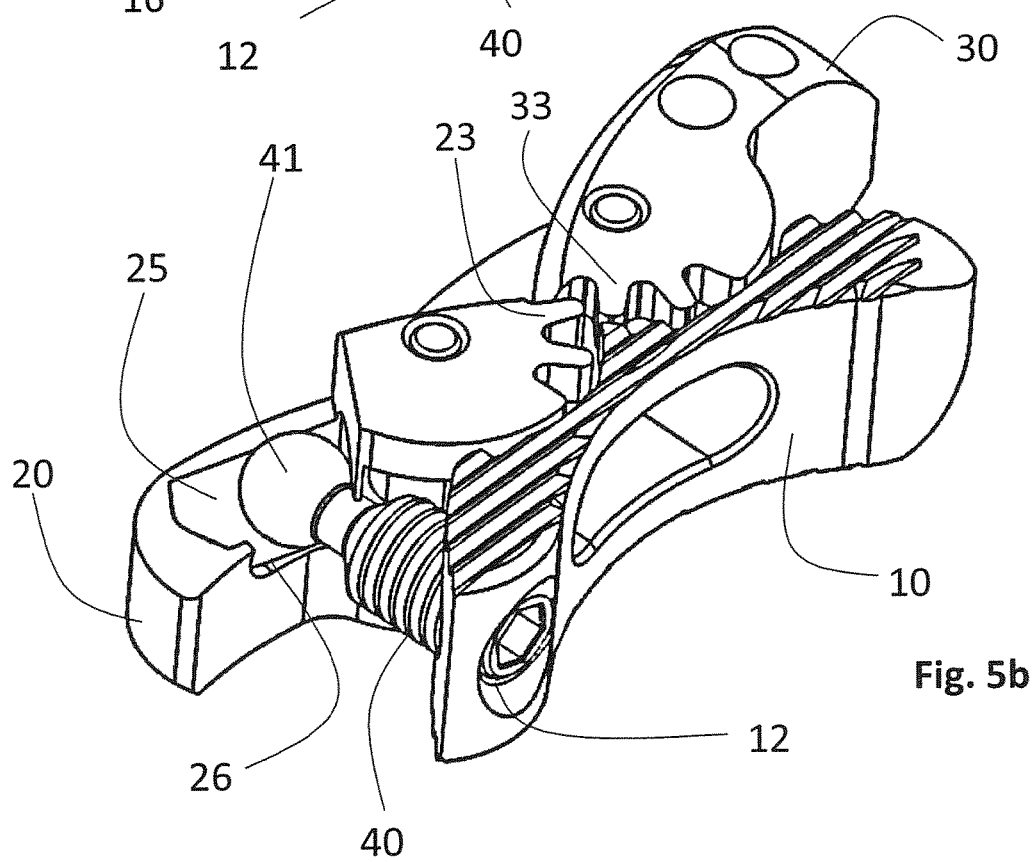

FIGS. 5a and 5b show the actuation mechanism of the expandable spinal implant 1 in more detail. In both figures, the first elongated implant member 20 is shown in a cut-away view.

In the first, unexpanded configuration of the expandable spinal implant 1, as shown in FIG. 5a, the ball head 41 of the dowel is located within the first channel 25 in a form-fitting manner. Linear movement of the dowel 40 within the second channel 12 will entail a rotational movement of the first elongated implant member 20 relative to the central base portion 10 by means of the interaction of the ball head 41 with the first channel 25. Further, the threaded shaft 42 comprises a drive 43. The threaded shaft 42 cooperates with the internal thread located in said first channel 12. By turning the dowel 40 via the drive 43, a linear translation of the dowel 40 will be caused by the cooperation of the threaded shaft 42 with the internal thread. Access to said drive 43 is made possible through the second channel 12, e.g. for a suitable instrument (not shown). In the embodiment shown, the drive 43 is configured as hexagonal drive, however, other drive types may also be used, such as e.g. a torx-drive. The base portion 10 further includes an attachment portion 16 configured to be coupled to an insertion instrument (not shown). In the initial configuration, the dowel 40 is located at a retracted position within the second channel 12 and protrudes out of central base portion 10.

FIG. 5b shows the expandable spinal implant 1 in the second, expanded configuration. In this configuration, the dowel 40 is located at an extended position within the second channel 12. By the translational movement of the dowel 40 from the retracted position as shown in FIG. 5a to said extended position, the ball head 41 pushed onto walls of the first channel 25 of the elongated member 20. This pushing force is translated in a rotational movement of the first elongated implant member 20, as its first end is coupled to the central base portion 10 by means of the first hinge-pin 60. Mediated by the engagement of the gear teeth 23, 33 the second elongated implant member 30 is likewise rotated.

The invention claimed is:

1. An expandable spinal implant comprising a first elongated implant members and a second elongated implant member, said elongated implant members being rotatably coupled to a central base portion, said implant members comprising a first end with an axis of rotation and circumferentially arranged gear teeth, wherein the gear teeth of said first elongated implant member are interlocked into said gear teeth of the second elongated implant member, wherein said base portion is a body in the form of a segmental arc and said elongated implant members are coupled to said base portion at an apex of said segmental arc.

2. The expandable spinal implant of claim 1, wherein the elongated implant members are in the shape of a segmental arc and substantially abut with said base portion along their entire length in an initial and unexpanded configuration.

3. The expandable spinal implant of claim 1, wherein said elongated implant members and the central base portion form a substantially X-shaped footprint in an expanded configuration.

4. The expandable spinal implant of claim 1, wherein the elongated implant members and the central base portion are substantially straight and form a substantially K-shaped footprint in an expanded configuration.

5. The expandable spinal implant of claim 1, comprising at least one pocket for receiving bone graft material.

6. The expandable spinal implant of claim 1, comprising elongated implant members of unequal length.

7. The expandable spinal implant of claim 1, comprising a dowel having a ball head at one end, said ball head cooperating with a first channel located on the inside of said first elongated implant member, such as to impart motion onto said first elongated implant member for rotating said first elongated implant member relative to said central base structure around its axis of rotation.

8. The expandable spinal implant according to claim 1, wherein the elongated implant members and the central base portion each comprise a lower surface and an upper surface, said upper surface and said lower surface of said elongated implant members and of said central base portion being flush with each other.

9. The expandable spinal implant according to claim 8, wherein the upper surfaces and the lower surfaces of said elongated implant members and of said central base portion being arranged at an angle to each other, said angle preferably being from 0° to 15°.

10. The expandable spinal implant according to claim 8, wherein the lower surfaces and the upper surfaces of said elongated implant members and of said central base portion are parallel to each other.

11. A kit comprising multiple expandable spinal implants of claim 1, wherein the expandable spinal implants have at least one of: incremental thicknesses between 8 and 20 mm, elongated implant members with varying lengths or elongated implant members with varying widths.

12. A kit according to claim 11, wherein the expandable spinal implants have varying angles between the lower surfaces and the upper surfaces of said elongated implant members and of said central base portion, said angles preferably varying from 1° to 15°.

* * * * *